(12) United States Patent
Rao et al.

(10) Patent No.: US 8,198,451 B2
(45) Date of Patent: Jun. 12, 2012

(54) PROCESS FOR THE SYNTHESIS OF MOXIFLOXACIN HYDROCHLORIDE

(75) Inventors: Dharmaraj Ramachandra Rao, Mumbai (IN); Rajendra Narayanrao Kankan, Mumbai (IN); Srinivas Laxminarayan Pathi, Bangalore (IN); Ravikumar Puppala, Bangalore (IN); Manish Gangrade, Mumbai (IN); Shashirekha Kanathala, Mumbai (IN)

(73) Assignee: CIPLA Limited, Mumbai (IN)

( * ) Notice: Subject to any disclaimer, the term of this patent is extended or adjusted under 35 U.S.C. 154(b) by 451 days.

(21) Appl. No.: 12/514,552

(22) PCT Filed: Nov. 13, 2007

(86) PCT No.: PCT/GB2007/004320
§ 371 (c)(1),
(2), (4) Date: Aug. 11, 2009

(87) PCT Pub. No.: WO2008/059223
PCT Pub. Date: May 22, 2008

(65) Prior Publication Data
US 2010/0152229 A1   Jun. 17, 2010

(30) Foreign Application Priority Data
Nov. 13, 2006   (IN) .................. 1879/MUM/2006

(51) Int. Cl.
C07D 215/38   (2006.01)
(52) U.S. Cl. ....................... 546/159; 514/312
(58) Field of Classification Search ............ 546/159; 514/312
See application file for complete search history.

(56) References Cited

U.S. PATENT DOCUMENTS

| | | | |
|---|---|---|---|
| 5,157,117 A | 10/1992 | Takagi et al. | |
| 5,849,752 A * | 12/1998 | Grunenberg et al. | 514/300 |
| 6,174,878 B1 * | 1/2001 | Gamache et al. | 514/211.12 |
| 6,235,908 B1 * | 5/2001 | Fey | 546/113 |
| 7,320,006 B2 * | 1/2008 | Bobbitt et al. | 707/760 |

FOREIGN PATENT DOCUMENTS

| | | |
|---|---|---|
| EP | 0350733 A2 | 6/1989 |
| EP | 0550903 A1 | 7/1993 |
| EP | 0657448 A1 | 6/1995 |
| EP | 0780390 A1 | 6/1997 |
| EP | 1832587 A1 | 9/2007 |
| ES | 2077490 A1 | 11/1995 |
| WO | 03014108 A1 | 2/2003 |
| WO | 2004091619 A1 | 10/2004 |
| WO | 2005012285 A1 | 2/2005 |
| WO | 2005054240 A1 | 6/2005 |
| WO | 2006134491 A2 | 12/2006 |
| WO | 2007010555 A2 | 1/2007 |
| WO | 2008059223 A2 | 5/2008 |
| WO | 2008059223 A3 | 5/2008 |

OTHER PUBLICATIONS

Foreign communication from the priority application—Invitation to Pay Additional Fees—PCT/GB2007/004320, Feb. 14, 2008, 6 pages.
Foreign communication from the priority application—International Preliminary Report on Patentability, PCT/GB2007/004320, May 19, 2009, 10 pages.
Foreign communication from the priority application—International Search Report and Written Opinion, PCT/GB2007/004320, Jun. 17, 2008, 14 pages.
Guo, Huiyuan, et al., "Preparation of 7-(aminomethylazaspiroheptyl)quinolinecarboxylic acid derivatives as bactercides," Database CA, Chemical Abstracts Service, Columbus OH, XP-002483125.

* cited by examiner

*Primary Examiner* — D M Seaman
(74) *Attorney, Agent, or Firm* — Conley Rose, P.C.; Rodney B. Carroll (57) ABSTRACT

A new polymorph of moxifloxacin hydrochloride is described, together with a method for making the polymorph. In addition, new intermediates in the formation of moxifloxacin hydrochloride are described, having formulas (1) and (II):

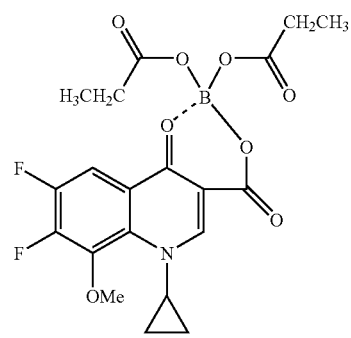

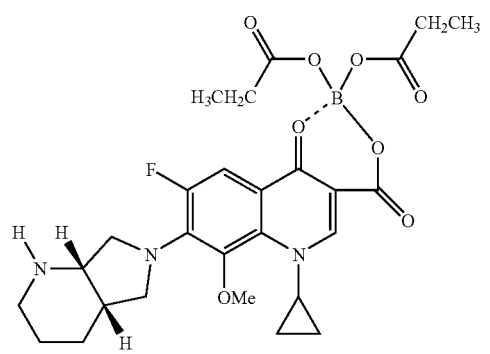

15 Claims, 4 Drawing Sheets

PROCESS FOR THE SYNTHESIS OF MOXIFLOXACIN HYDROCHLORIDE

CROSS-REFERENCE TO RELATED APPLICATIONS

This application is a filing under 35 U.S.C. 371 of International Application No. PCT/GB2007/004320 filed Nov. 13, 2007, entitled "Process for the Synthesis of Moxifloxacin Hydrochloride," claiming priority of Indian Patent Application No. 1879/MUM/2006 filed Nov. 13, 2006, which applications are incorporated by reference herein in their entirety.

FIELD OF THE INVENTION

The present invention relates to a process for the preparation of moxifloxacin, and more particularly relates to a process for the preparation of moxifloxacin which uses a novel Borate intermediate. The present invention relates to a novel crystalline form of moxifloxacin hydrochloride and process to prepare the same.

BACKGROUND OF THE INVENTION

Moxifloxacin hydrochloride {1-cyclopropyl-7-[S,S]-2,8-diazabicyclo-[4,3,0]non-8-yl)6-fluoro-1,4-dihydro-8-methoxy-4-oxo-3-quinoline carboxylic acid hydrochloride} is known from EP 350733 & EP 550903 and has the following chemical structure.

Moxifloxacin Hydrochloride

Moxifloxacin is a fluoroquinolone broad spectrum antibacterial agent, shown to be clinically active against Gram-positive microorganisms including *staphylococcus aureus, streptococcus pneumonia,* and *streptococcus pyogenes*; significantly better than those of Sparfloxacin and Ciprofloxacin that was disclosed in EP No 350,733 and EP No 550,903. Moxifloxacin also has activity against Gram-negative microorganisms including *haemophilus influenzae, haemophilus parainfluenzae, klebisiella pneumoniae,* and *moraxella catarrhalis.*

The prior art disclosed in European patent No's EP 350,733, EP 550,903 and EP 657,448 describes the preparation of moxifloxacin hydrochloride involving the condensation of 1-cyclopropyl-6,7-difluoro-8-methoxy-4-oxo-1,4-dihydro-3-quinoline carboxylic acid or its esters with (S,S)2,8-diazabicyclo[4.3.0]nonane in presence of a base and its conversion to hydrochloride at higher temperatures leading to the desired moxifloxacin along with its potential isomer namely (4aS-Cis)-1-cyclopropyl-6-(2,8-diazabicyclo[4.3.0]non-8-yl)-7-fluoro-8-methoxy-4-oxo-1,4-dihydro-3-quinoline carboxylic acid as a major impurity. As the impurity and moxifloxacin are positional isomers they are difficult to separate. Further, purification of moxifloxacin to remove this isomer results in lower yields thereby increasing the product cost.

U.S. Pat. No. 5,849,752 discloses the monohydrate of moxifloxacin hydrochloride{1-cyclopropyl-7-[S,S]-2,8-diazabicyclo-[4,3,0]non-8-yl)-6-fluoro-1,4-dihydro-8-methoxy-4-oxo-3-quinoline carboxylic acid hydrochloride} (CDCH) and its preparation by treating the anhydrous crystalline form with ethanol/water mixtures.

Moxifloxacin hydrochloride exhibits polymorphism. WO 2004/091619 discloses a new crystalline Form III of moxifloxacin monohydrochloride and processes for making the crystalline form using an alkanol and an antisolvent for precipitation. This patent discloses X-ray powder diffraction patterns, $^{13}C$ solid state NMR spectra, Differential scanning calorimetry (DSC) thermogram and IR spectrum of the crystalline form III.

However, it is known that polymorphic forms of the same drug may have substantial difference in certain pharmaceutically important properties such as dissolution characteristics and bioavailability as well as stability of the drug. Furthermore, different crystalline form may have different particle size, hardness and glass transition temperature. Thus, one crystalline form may provide significant advantages over other crystalline forms of the same drug in solid dosage form manufacture processes, such as accurate measurement of the active ingredients, easier filtration, or improved stability during granulation or storage. Furthermore, a particular process suitable for one crystalline form may also provide drug manufacturers several advantages such as economically or environmentally suitable solvents or processes, or higher purity or yield of the desired product.

U.S. Pat. No. 5,157,117 discloses (1-cyclopropyl-6,7-difluoro-8-methoxy-4-oxo-1,4-dihydro-3-quinoline carboxylic acid-$O^3,O^4$)bis(acyloxy-O)borate and a process for its preparation by reacting ethyl-1-cyclopropyl-6,7-difluoro-8-methoxy-4-oxo-1,4-dihydro-3-quinoline carboxylate with Boric acid and acetic anhydride in presence of zinc chloride and its conversion to Gatifloxacin hydrochloride.

WO 2005/012285 discloses the process for the preparation of moxifloxacin hydrochloride using a novel intermediate namely (4aS-Cis)-(1-cyclopropyl-7-(2,8-diazabicyclo[4,3,0] non-8-yl)-6-fluoro-8-methoxy-4-oxo-1,4-dihydro-3-quinoline carboxylic acid-$O^3,O^4$)bis(acycloxy-O)borate. The disclosure further refers to the preparation of moxifloxacin hydrochloride pseudohydrate and conversion to moxifloxacin hydrochloride monohydrate. The fingerprinting of the novel intermediate, moxifloxacin hydrochloride pseudohydrate and moxifloxacin hydrochloride anhydrous and moxifloxacin hydrochloride monohydrate forms are substantiated using NMR, FTIR and X-ray diffraction analysis.

Prior art processes for the preparation of the Borate complex without use of catalyst has its limitations owing to higher exothermicity during acetylation thereby reducing the reaction purity which is indicated in the lower yields obtained when further converted to moxifloxacin after condensation with nonane and subsequent hydrolysis. Also prior art makes use of triethyl amine as a base required for the condensation step with nonane.

Hence it is a long felt need of the industry to provide a simple, safe and cost effective process that produces moxifloxacin hydrochloride with high product yield and quality.

SUMMARY OF THE INVENTION

In one aspect, invention relates to a new crystalline form of moxifloxacin hydrochloride designated herein as Form C. The invention also relates to a method of making the new form and to pharmaceutical compositions containing it.

In another aspect the invention relates to new intermediates for use in making moxifloxacin and salts thereof, of formulas (1) and (2):

The invention also relates to method of making the intermediates (1) and (II).

According to an aspect of the invention there is provided a method of making a compound of formula (I), comprising reacting propionic anhydride and boric acid with Ethyl-1-cyclopropyl-6-7-difluoro-8-methoxy-4-oxo-1,4-dihydro-3-quinolone carboxylate, preferably without the use of any catalyst, to obtain the compound of formula (I).

According to an aspect of the invention there is provided a method of making a compound of formula (II), as defined in claim 20, comprising condensing a compound of formula (I), as defined in claim 18, with (S,S)-2,8-Diazabicyclo[4.3.0] nonane in an organic solvent, preferably in the absence of a base, to obtain the compound of formula (II).

BRIEF DESCRIPTION OF THE DRAWINGS

Reference is made to the accompanying drawings, in which.

DETAILED DESCRIPTION OF THE INVENTION

The present invention provides an improved process for the preparation of moxifloxacin base, or a salt thereof, especially the hydrochloride salt, using a novel intermediate (I) and (II).

In one embodiment of the present invention the process comprises first reacting boric acid and propionic anhydride with ethyl 1-cyclopropyl-6,7-difluoro-8-methoxy-4-oxo-1,4-dihydro-3-quinolinecarboxylate (A) without using any catalyst to give a novel borate complex of formula (I), 1-cyclopropyl-6,7-difluoro-8-methoxy-4-oxo-1,4-dihydro-3-quinoline carboxylic acid-$O^3,O^4$)bis(propyloxy-O)borate.

Boric acid     Propionic anhydride     Boron tripropionate

+

(I)

(A)

In another embodiment of the present invention the novel borate complex (I) may be condensed with (S,S)-2,8-Diazabicyclo[4.3.0]nonane (B) in absence of any base using an organic polar solvent to give novel intermediate of formula (II).

The intermediate (II) may be subjected to hydrolysis to get moxifloxacin base. The base may be treated with hydrochloric acid in the presence of a suitable solvent to give moxifloxacin hydrochloride.

(MOXIFLOXACIN HYDROCHLORIDE)

Surprisingly, it was found that use of propionic anhydride without the use of any catalyst during the preparation of Borate complex follows a nonexothermic pathway resulting in lesser impurity formation and hence better recovery of the product. Also reaction of the propionate complex with the nonane (B) without the use of a base results in moxifloxacin with excellent yields. In general, we prefer that a base is used if the temperature of the reaction is less than or equal to about 100° C. We prefer that a base is used if the temperature of the reaction is above 100° C.

The process of present invention wherein the novel borate complex (I) is condensed with (S,S)-2,8-Diazabicyclo[4.3.0] nonane (B) can be optionally carried out in using sodium methoxide, triethyl amine as base in an organic polar solvent to give novel intermediate of formula (II).

The yield of moxifloxacin hydrochloride is much higher compared with the yields from prior art processes: 100.0 g of nonane yields 260.0 g of moxifloxacin hydrochloride using the process of the present invention whereas; 100.0 g of nonane yields 187.0 g of moxifloxacin hydrochloride as per prior art process.

In yet another aspect the present invention provides a novel crystalline form of moxifloxacin hydrochloride herein designated Form C, and a process for the preparation of Form C which comprises the step of: dissolving or suspending the moxifloxacin base in methanol treating with methanolic hydrochloric acid, preferably at a temperature range of 0° C. to 30° C., and isolating moxifloxacin hydrochloride form C from methanol.

It is preferred that the methanol is substantially pure, i.e., it has a water content less than 0.5 wt %.

It is preferred that the methanolic hydrochloride comprises 10-15% HCl gas dissolved in methanol.

Figure 1:
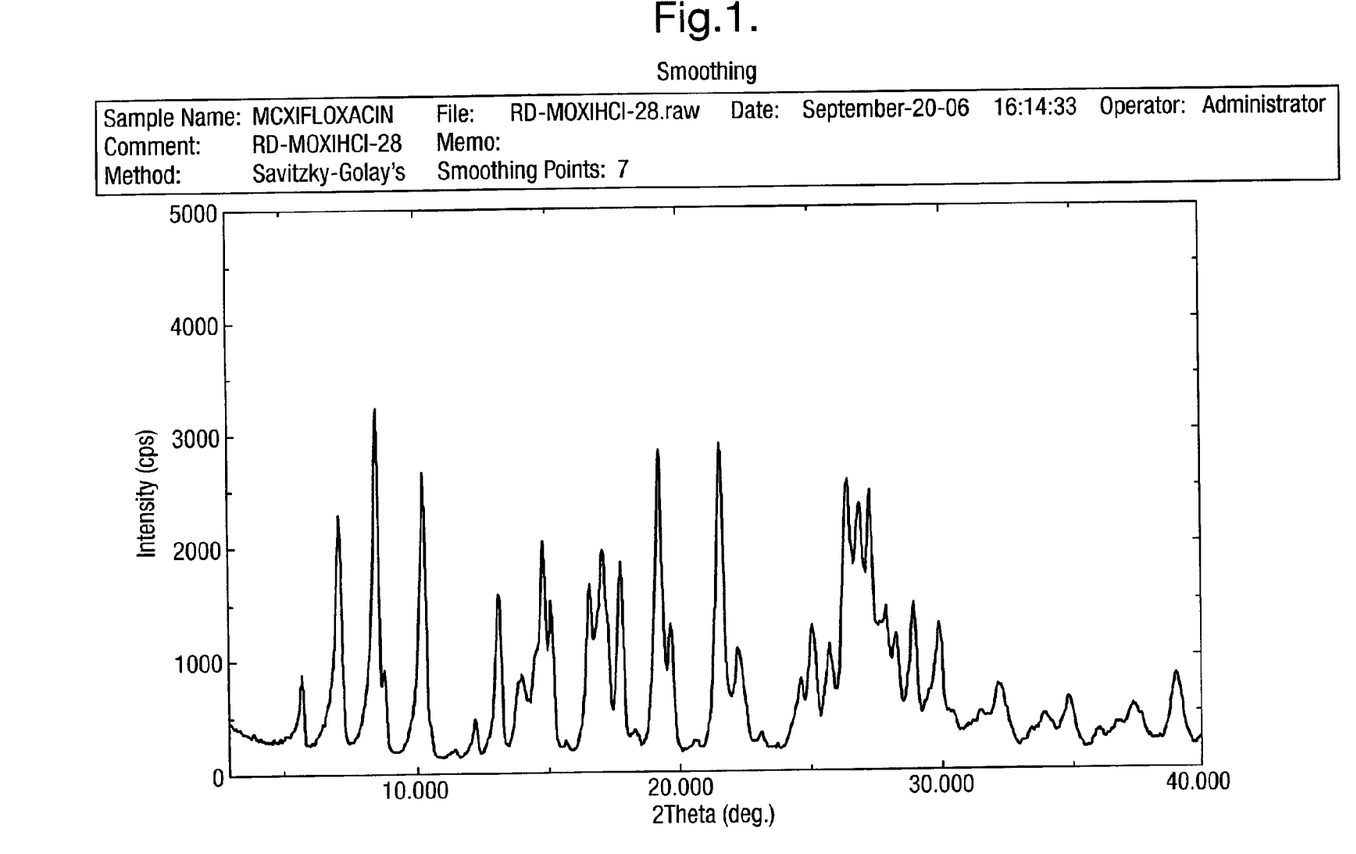
FIG. 1 is an X-ray diffraction pattern of moxifloxacin hydrochloride Form C.

The moxifloxacin base may be formed according to the processes described above, specifically:
i) Reacting Propionic anhydride and boric acid with Ethyl-1-cyclopropyl-6-7-difluoro-8-methoxy-4-oxo-1,4-dihydro-3-quinolone carboxylate (A) to obtain 1-cyclopropyl-6,7-difluoro-8-methoxy-4-oxo-1,4-dihydro-3-quinoline carboxylic acid-$O^3,O^4$ bis(propyloxy-O)borate (I);

ii) Condensing the borate complex (I) with nonane (B) in the absence of a base and in an organic solvent to obtain a novel intermediate (4aS-Cis)-(1-cyclopropyl-7-(2,8-diazabicyclo[4.3.0]non-8-yl)-6-fluoro-8-methoxy-4-oxo-1,4-dihydro-3-quinoline carboxylic acid-$O^3,O^4$)bis(propyloxy-O)borate (II); and iii) hydrolysing the intermediate (II) to get moxifloxacin base Moxifloxacin Hydrochloride Form C according to the present invention is further characterized by X-ray powder diffraction spectrum as obtained by X-ray powder diffraction spectrum measured on a Rigaku D-maz-2200 advance X-ray powder diffractometer having a copper-k-α radiation as shown in FIG. 1.

Moxifloxacin Hydrochloride Form C is further characterized by having characteristic peaks (2 θ°) at least at 15.080, 27.86, and 28.221±0.2 θ°. The peaks are shown in more detail in Table 1.

TABLE 1

| 2 THETA VALUES | I/I$_0$ |
| --- | --- |
| 5.72 | 21.3 |
| 7.139 | 68.6 |
| 8.499 | 100 |
| 8.779 | 23.7 |
| 10.24 | 85.8 |
| 12.20 | 10.9 |
| 13.139 | 45.4 |
| 13.98 | 23.5 |
| 14.50 | 31.6 |
| 14.799 | 61.8 |
| 15.08 | 46.6 |
| 16.52 | 49.8 |
| 17.04 | 59.6 |
| 17.219 | 41.1 |
| 17.74 | 54.4 |
| 19.239 | 87.5 |
| 19.679 | 37.3 |
| 21.54 | 92.6 |
| 22.22 | 29.8 |
| 24.60 | 20.9 |
| 25.06 | 37.2 |
| 25.72 | 31.4 |
| 26.42 | 65.7 |
| 26.88 | 61 |
| 27.260 | 64.4 |
| 27.86 | 27.9 |
| 28.221 | 23.2 |
| 28.882 | 30.5 |
| 29.859 | 30.1 |
| 31.461 | 7.5 |
| 32.101 | 16.7 |
| 33.420 | 5.6 |
| 33.879 | 10.8 |
| 34.860 | 15.3 |
| 36.659 | 7.8 |
| 37.299 | 12.2 |
| 37.638 | 9.8 |
| 38.981 | 21.8 |

Furthermore, the following Table 2 shows in more detail the data for the XRPD shown in FIG. 1.

TABLE 2

[RD-MOXIHCl-28.raw] MOXIFLOXACIN - RD-MOXIHCl-28
Peak Search Report

| # | 2-Theta | d(Å) | Height | Height % | FWHM |
| --- | --- | --- | --- | --- | --- |
| 1 | 5.720 | 15.4388 | 381 | 21.3 | 0.216 |
| 2 | 6.504 | 13.5794 | 120 | 6.7 | 0.489 |
| 3 | 7.139 | 12.3714 | 1225 | 68.6 | 0.332 |
| 4 | 8.499 | 10.3947 | 1786 | 100.0 | 0.294 |
| 5 | 8.779 | 10.0639 | 423 | 23.7 | 0.442 |
| 6 | 10.241 | 8.6305 | 1532 | 85.8 | 0.269 |
| 7 | 12.201 | 7.2482 | 195 | 10.9 | 0.153 |
| 8 | 13.139 | 6.7329 | 810 | 45.4 | 0.238 |
| 9 | 13.980 | 6.3297 | 420 | 23.5 | 0.662 |
| 10 | 14.501 | 6.1035 | 564 | 31.6 | 1.105 |
| 11 | 14.799 | 5.9811 | 1104 | 61.8 | 0.611 |
| 12 | 15.080 | 5.8703 | 821 | 46.0 | 0.458 |
| 13 | 16.522 | 5.3610 | 889 | 49.8 | 0.564 |
| 14 | 17.040 | 5.1991 | 1064 | 59.6 | 0.542 |
| 15 | 17.219 | 5.1456 | 734 | 41.1 | 0.987 |
| 16 | 17.740 | 4.9957 | 972 | 54.4 | 0.303 |
| 17 | 19.239 | 4.6097 | 1563 | 87.5 | 0.367 |
| 18 | 19.679 | 4.5075 | 666 | 37.3 | 0.401 |
| 19 | 21.540 | 4.1221 | 1654 | 92.6 | 0.391 |
| 20 | 22.220 | 3.9975 | 533 | 29.8 | 0.708 |
| 21 | 24.601 | 3.6156 | 374 | 20.9 | 0.455 |
| 22 | 25.060 | 3.5505 | 665 | 37.2 | 0.376 |
| 23 | 25.720 | 3.4609 | 560 | 31.4 | 0.371 |
| 24 | 26.420 | 3.3707 | 1174 | 65.7 | 0.606 |
| 25 | 26.880 | 3.3141 | 1089 | 61.0 | 0.813 |
| 26 | 27.260 | 3.2688 | 1150 | 64.4 | 1.072 |
| 27 | 27.860 | 3.1997 | 499 | 27.9 | 0.843 |
| 28 | 28.221 | 3.1596 | 414 | 23.2 | 0.273 |
| 29 | 28.882 | 3.0888 | 545 | 30.5 | 0.222 |
| 30 | 29.859 | 2.9899 | 538 | 30.1 | 0.327 |
| 31 | 31.003 | 2.8821 | 43 | 2.4 | 0.584 |
| 32 | 31.461 | 2.8412 | 134 | 7.5 | 1.031 |
| 33 | 32.101 | 2.7860 | 298 | 16.7 | 0.707 |
| 34 | 33.420 | 2.6790 | 100 | 5.6 | 0.509 |
| 35 | 33.879 | 2.6437 | 193 | 10.8 | 0.684 |
| 36 | 34.860 | 2.5716 | 273 | 15.3 | 0.522 |
| 37 | 36.659 | 2.4494 | 140 | 7.8 | 0.933 |
| 38 | 37.299 | 2.4088 | 217 | 12.2 | 0.837 |
| 39 | 37.638 | 2.3879 | 175 | 9.8 | 1.534 |
| 40 | 38.981 | 2.3086 | 390 | 21.8 | 0.415 |

SCAN: 3.0/40.0/0.02/0.6(sec), Cu(40 kV, 30 mA), I(max) = 1933. Sep. 20, 2006 16:33
PEAK: 15-pts/Parabolic Filter, Threshold = 2.0, Cutoff = 1.5%, BG = 4/2.0, Peak − Top = Summit
NOTE:
Intensity = Counts, 2T(0) = 0.0(deg), Wavelength to Compute d-Spacing = 1.54056 Å (Cu/K-alpha1)

Figure 2:
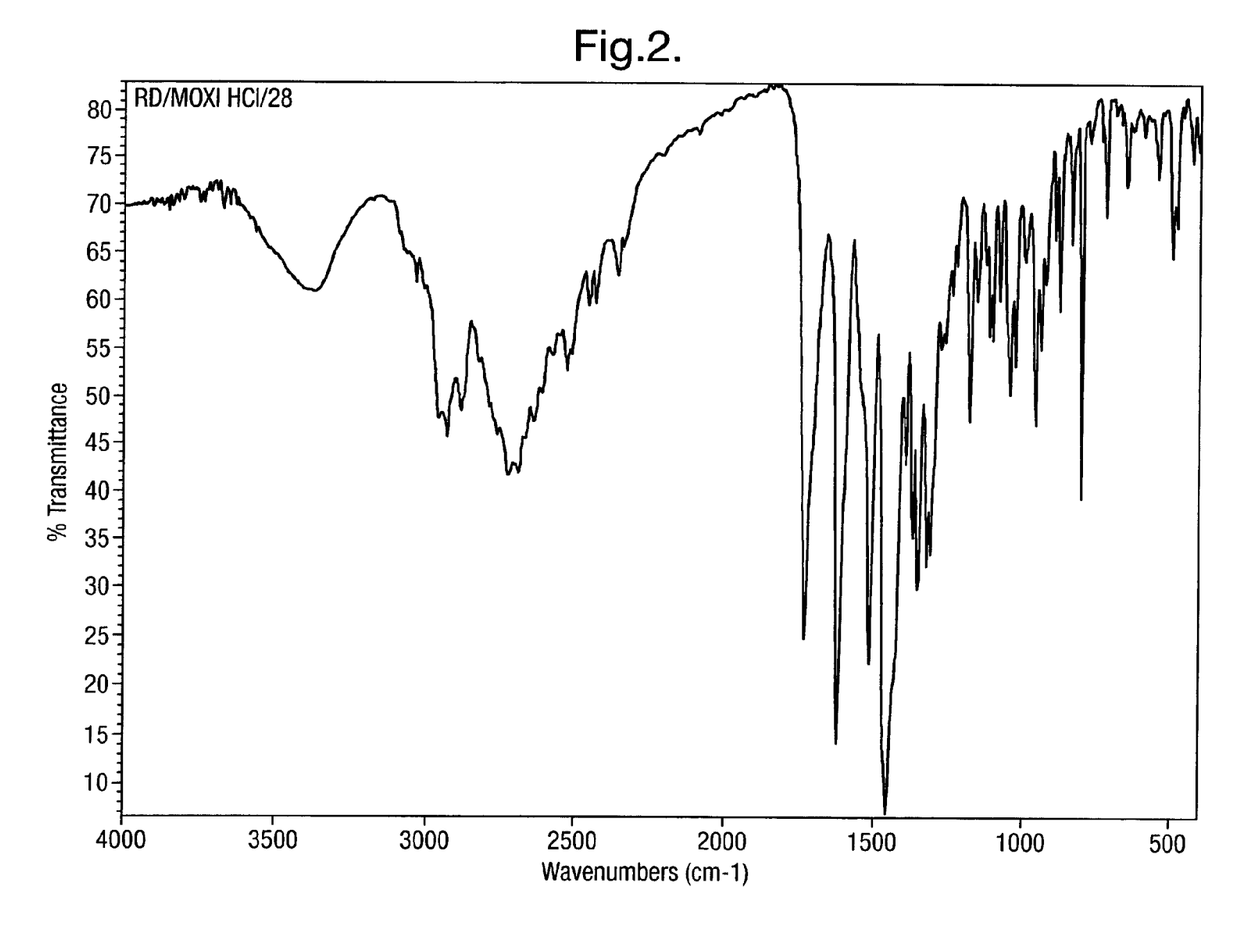
FIG. 2 is a FTIR of moxifloxacin hydrochloride Form C.
Figure 3:
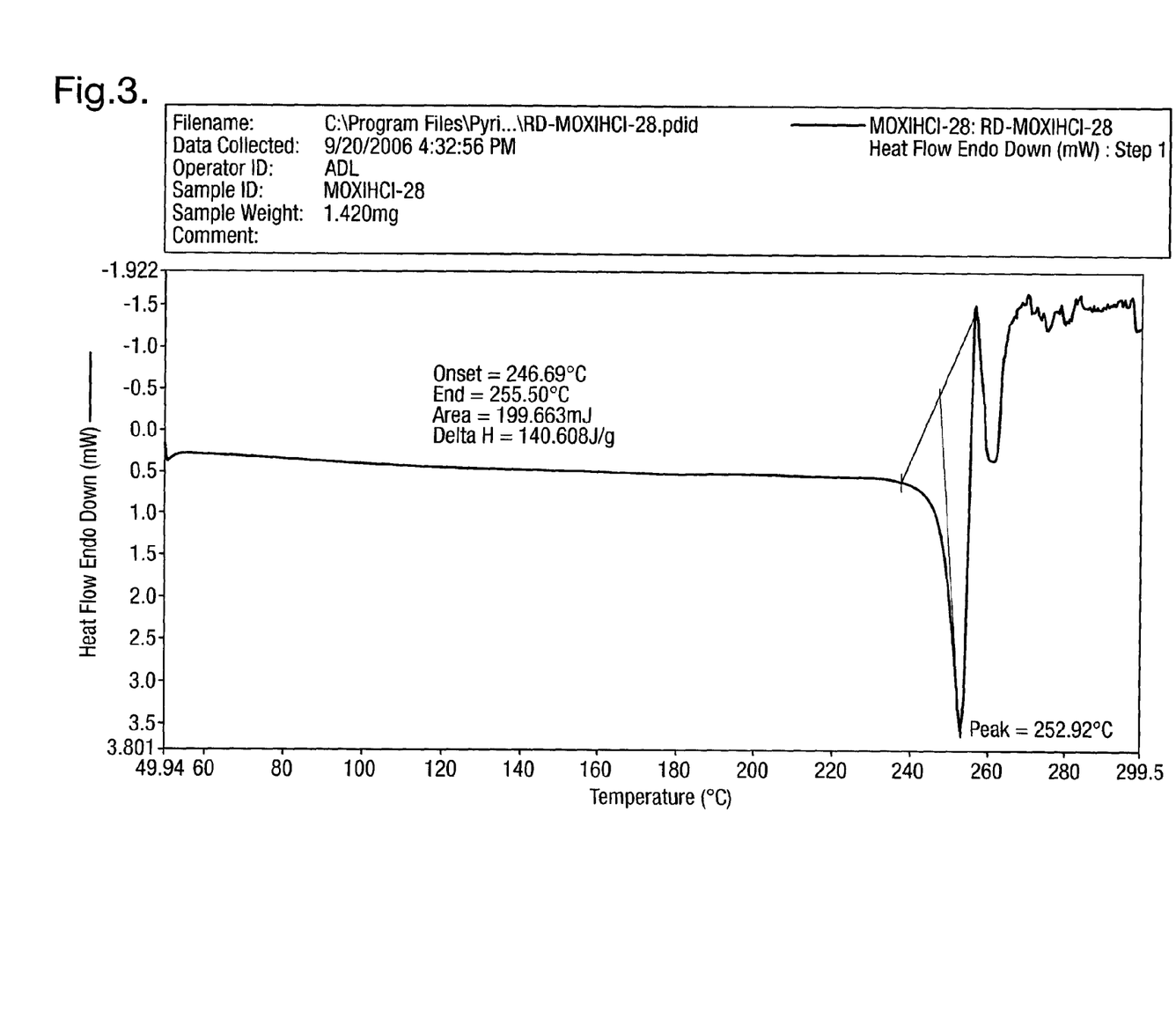
FIG. 3 is a differential scanning calorimetry (DSC) of moxifloxacin hydrochloride Form C.
Figure 4:
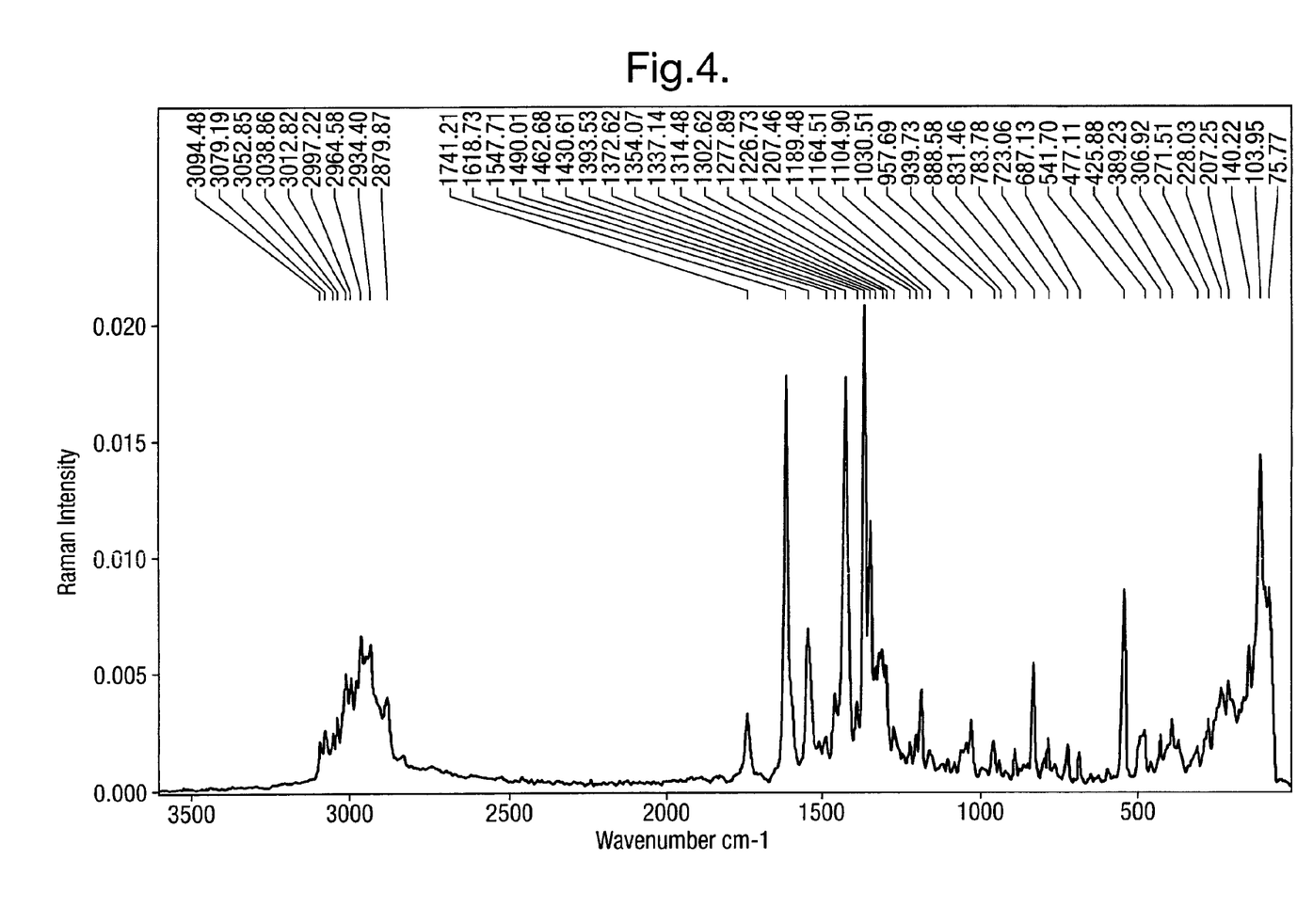
FIG. 4 is a Raman Spectra of moxifloxacin hydrochloride Form C.

Moxifloxacin Hydrochloride Form C according to the present invention is further characterized by IR, DSC, and Raman as shown respectively in FIGS. 2, 3 and 4.

In the IR spectrum of moxifloxacin hydrochloride Form C, the wave number of several distinctive peaks may help to identify the crystalline nature of the compound. These IR peaks measured on IR Thermo Nicolet instrument includes absorption bands at about 3367 $cm^{-1}$; 2931 $cm^{-1}$; 2885 $cm^{-1}$; 2728 $cm^{-1}$; 2691 $cm^{-1}$; 1733 $cm^{-1}$; 1311 $cm^{-1}$; 1242 $cm^{-1}$; 1104 $cm^{-1}$; 923 $cm^{-1}$.

Moxifloxacin Hydrochloride Form C according to the present invention is further characterized by DSC having a melting endotherm peak at 253° C. The DSC spectrum was measured on Perkin Elmer Diamond DSC.

Moxifloxacin Hydrochloride Form C according to the present invention is further characterized by Raman Spectra having Raman peaks at 3094.48, 3079.19, 3052.84, 3038.86, 3012.81, 2997.21, 2964.58, 2934.40, 2879.86, 1741.20, 1618.72, 1547.70, 1490.01, 1462.68, 1430.60, 1393.53, 1372.62, 1354.07, 1337.13, 13124.47, 1302.62, 1277.88, 1226.72, 1207.46, 1189.47, 1164.50, 1104.89, 1030.51, 957.69, 939.73, 888.57, 831.46, 783.78, 723.06, 687.13, 541.70, 477.11, 425.87, 389.22, 306.92, 271.51, 228.03, 207.24, 140.22, 103.95, 75.76. cm$^{-1}$. The Raman spectra is done on the instrument Bruker RFS-100S.

The invention also relates to pharmaceutical compositions comprising moxifloxacin hydrochloride Form C. It can be formulated with one or more pharmaceutically acceptable carriers, also known as excipients, which ordinarily lack pharmaceutical activity, but have various useful properties which may, for example, enhance the stability, sterility, bioavailability, and ease of formulation of a pharmaceutical composition. These carriers are pharmaceutically acceptable, meaning that they are not harmful to humans or animals when taken appropriately and are compatible with the other ingredients in a given formulation. The carriers may be solid, semi-solid, or liquid, and may be formulated with the compound in bulk. The resulting mixture may be manufactured in the form of a unit-dose formulation (i.e., a physically discrete unit containing a specific amount of active ingredient) such as tablet or capsule.

In another aspect, the invention also provides methods of treating infections caused by susceptible strains of *staphylococcus aureus, streptococcus pneumoniae*, and *streptococcus pyogenes, haemophilus influenzae, haemophilus parainfluenzae, klebsiella pneumoniae*, and *moraxella catarrhalis* which includes administering a mammal in need thereof an effective amount of the moxifloxacin hydrochloride Form C.

EXAMPLES

The examples which will follow will further illustrate the preparation of the compound of the invention, according to different process routes and including new intermediates. These examples are not intended to limit the scope of the invention as defined hereinabove or as claimed below in any way.

Example 1

Propionic anhydride (200.0 g) was heated to 80-85° C. and boric acid (30.0 g) was added at a temperature range of 80-90° C., refluxed for 2 hours, and later cooled to 70° C. Ethyl-1-cyclopropyl-6-7-difluoro-8-methoxy-4-oxo-1,4-dihydro-3-quinolone carboxylate (100 g) was added under stirring. The reaction mass temperature was raised to 100° C. and maintained for 4 hours at 100° C. After the completion of reaction the reaction mass was cooled to 0° C., purified water (1000.0 ml) was slowly added at 0° C. and maintained for 1 hour at 0-5° C. The product was filtered, washed with water (400.0 ml) and dried at 45-50° C. in Fluid bed drier to get 135.0 g (96.0%) of 1-cyclopropyl-6,7-difluoro-8-methoxy-4-oxo-1,4-dihydro-3-quinoline carboxylic acid-O$^3$,O$^4$ bis(propyloxy-O)borate.

Example 2

1-cyclopropyl-6,7-difluoro-8-methoxy-4-oxo-1,4-dihydro-3-quinoline carboxylic acid-O$^3$,O$^4$ bis(propyloxy-O)borate (100.0 g) was suspended in n-butanol (500.0 ml) to which (S,S)-2,8-diazabicyclo(4,3,0)nonane (29.0 g) diluted with 100.0 ml n-butanol was added slowly at 10-15° C. The contents were heated to 100° C. and maintained for 3 hours. After the completion of reaction it was cooled to 25-30° C. 200.0 ml methanol was added and pH was adjusted 1.0-2.0 using methanolic hydrochloric acid. The contents were stirred at 25-30° C. for 2 hours. After completion of reaction the reaction mass was distilled to residue. Purified water 500 ml was added and pH was adjusted to 7.5-9.0 using liquor ammonia. The reaction mass was then extracted with dichloromethane. The organic layer was dried using sodium sulphate and concentrated to residue. The residue was stripped with 100 ml methanol. 300 ml methanol was charged and pH was adjusted to 1.0-2.0 using methanolic hydrochloric acid, the contents were further cooled to 0-5° C. and maintained for 1 hour. The solid was filtered and washed with chilled methanol (50.0 ml) and dried under vacuum at 85-90° C. to yield 75.0 g (75%) of moxifloxacin hydrochloride.

Example 3

1-cyclopropyl-6,7-difluoro-8-methoxy-4-oxo-1,4-dihydro-3-quinoline carboxylic acid-O$^3$,O$^4$ bis(propyloxy-O)borate (100.0 g) was suspended in acetonitrile (445.0 ml). (S,S)-2,8-diazabicyclo(4,3,0)nonane (29.0 g) diluted with 50.0 ml acetonitrile. The contents were heated to reflux temperature optionally in presence of triethyl amine and maintained for 2 hours. The reaction mass was distilled under vacuum to residue. Diisopropyl ether (500.0 ml) was added and the contents were cooled to 25-30° C. The resulting product was filtered and washed with diisopropyl ether (50.0 ml) and dried at 45-50° C. under vacuum to yield 120.0 g (93.8%) of (4aS-Cis)-1-Cyclopropyl-7-(2,8 diazabicyclo[4.3.0]non-8-yl)-6-fluoro-8-methoxy-4-oxo-1,4-dihydro-3-quinoline carboxylic aid-O$^3$,O$^4$) bis(propyloxy-O)borate.

Example 4

(4aS-Cis)-1-Cyclopropyl-7-(2,8 diazabicyclo[4.3.0]non-8-yl)-6-fluoro-8-methoxy-4-oxo-1,4-dihydro-3-quinoline carboxylic aid-O$^3$,O$^4$)bis(propyloxy-O)borate (100.0 g), was suspended in 500.0 ml methanol and pH was adjusted to 1.0-2.0 using hydrochloric acid. The reaction mass was maintained at 10-15° C. for 2 hours. The reaction mass was distilled to obtain a residue. Purified water 500.0 ml was added and pH was adjusted to 7.5-8.0 using liquour ammonia. The contents were stirred for 15 minutes and heated to 70-75° C. The reaction mass was then cooled to 25-30° C. and stirred for 1 hour. The resulting solid were filtered and washed with purified water and dried under vacuum at 55-60° C. to obtain 65.0 g (90%) moxifloxacin base.

Example 5

The (4aS-Cis)-1-Cyclopropyl-7-(2,8 diazabicyclo[4.3.0]non-8-yl)-6-fluoro-8-methoxy-4-oxo-1,4-dihydro-3-quinoline carboxylic acid-O$^3$,O$^4$)bis(propyloxy-O)borate (100.0 g), was suspended in about 500.0 ml methanol and pH was adjusted to 1.0-2.0 using hydrochloric acid and stirred at 10-15° C. for 2 hours. The reaction mass was distilled to residue. Purified water 500.0 ml was added and pH was adjusted to 7.5-8.0 using liquour ammonia. The reaction mass was extracted with 500.0 ml methylene chloride and organic layer was washed with 70.0 ml purified water, dried over sodium sulphate. The organic layer was distilled under vacuum, stripped off with 200.0 ml methanol. Methanol 200.0 ml was added and chilled to 0-5° C. and stirred for 1 hour. The resulting solid was filtered and washed with chilled methanol and dried under vacuum at 55-60° C. to obtain 65.0 g (90%) moxifloxacin base.

Example 6

Moxifloxacin base 50.0 g was stirred in 200.0 ml methanol for 10-15 minutes at 25-3-° C. The pH was adjusted to 1.0-2.0 using methanolic hydrochloric acid. The reaction mass was chilled to 0-5° C. and maintained for 1 hour. The solids were filtered and dried under vacuum at 85-90° C. to yield 52.5 g (105%) of moxifloxacin hydrochloride.

Example 7

1-cyclopropyl-6,7-difluoro-8-methoxy-4-oxo-1,4-dihydro-3-quinoline carboxylic acid-$O^3,O^4$ bis(propyloxy-O)borate (100.0 g) was suspended in acetonitrile (445.0 ml). (S,S)-2,8-diazabicyclo(4,3,0)nonane (29.0 g) diluted with 50.0 ml acetonitrile was slowly added at 10-15° C. followed by triethyl amine (25.0 g). The contents were heated to reflux temperature for 2 hours. Cooled to 25-30° C. Methanol (200.0 ml) was added and pH was adjusted to 1.0-2.0 using hydrochloric acid and stirred at 10-15° C. for 2 hours. After the completion of reaction, the reaction mass was concentrated to residue. Purified water 500.0 ml was added and pH was adjusted to 7.5-9.0 using liquour ammonia under stirring. The contents were heated to 70-75° C. and ammonia is expelled off by purging Nitrogen gas to the reaction mass. The reaction mass was cooled to 25-30° C. and stirred for 1 hour. The resulting solid was filtered and washed with purified water and dried under vacuum at 55-60° C. to obtain 75.0 g moxifloxacin base. 70.0 g of moxifloxacin base was stirred with 350.0 ml of methanol at 25-30°. The pH was adjusted to 1.0-2.0 using methanolic hydrochloric acid and contents were chilled to 0-5° C. and stirred for 1 hour at the same temperature. The solid was filtered and dried under vacuum at 85-90° C. to yield 78.0 g (77%) of moxifloxacin hydrochloride.

Example 8

Moxifloxacin hydrochloride 100.0 gm was stirred with methanol 800.0 ml and triethyl amine 25-30° C. The reaction mass was concentrated partially. Further 300.0 ml of methanol was added and the pH was adjusted to 1.0-2.0 using hydrochloric acid gas dissolved in methanol at 20-25° C. The contents were cooled to 0-5° C. and maintained at 0-5° C. for 2 hours. The resulting solids were filtered and washed with 50.0 ml chilled methanol. The product was dried under vacuum at 80-90° C. to obtain 90-95.0 gm of moxifloxacin hydrochloride Form C.

It will be appreciated that the invention described above may be modified within the scope of the claims.

The invention claimed is:

1. Moxifloxacin hydrochloride Form C characterized by having an XRPD with peaks at 15.08, 27.86 and 28.22° 2θ±0.2° 2θ.

2. Moxifloxacin hydrochloride Form C according to claim 1, characterized by having an XRPD with peaks at 10.24, 15.08, 17.21, 24.60, 25.06, 26.42, 27.86, 28.22, 28.88 and 29.85±0.2° 2θ.

3. Moxifloxacin hydrochloride Form C according to claim 1, characterized by having an XRPD with peaks as shown in the following table:

| °2θ ± 0.2 °2θ |
|---|
| 5.72 |
| 7.139 |
| 8.499 |
| 8.779 |
| 10.24 |
| 12.20 |
| 13.139 |
| 13.98 |
| 14.50 |
| 14.799 |
| 15.08 |
| 16.52 |
| 17.04 |
| 17.219 |
| 17.74 |
| 19.239 |
| 19.679 |
| 21.54 |
| 22.22 |
| 24.60 |
| 25.06 |
| 25.72 |
| 26.42 |
| 26.88 |
| 27.260 |
| 27.86 |
| 28.221 |
| 28.882 |
| 29.859 |
| 31.461 |
| 32.101 |
| 33.420 |
| 33.879 |
| 34.860 |
| 36.659 |
| 37.299 |
| 37.638 |
| 38.981 |

4. Moxifloxacin hydrochloride Form C according to claim 1, characterized by having an XRPD as shown in FIG. 1.

5. Moxifloxacin hydrochloride Form C characterized by having an infrared spectrum with peaks indicated at about 3367 $cm^{-1}$; 2931 $cm^{-1}$; 2885 $cm^{-1}$; 2728 $cm^{-1}$; 2691 $cm^{-1}$; 1733 $cm^{-1}$; 1311 $cm^{-1}$; 1242 $cm^{-1}$; 1104 $cm^{-1}$; 923 $cm^{-1}$.

6. Moxifloxacin hydrochloride Form C according to claim 5, characterized by having and infrared spectrum as shown in FIG. 2.

7. Moxifloxacin hydrochloride Form C characterized by having a differential scanning calorimetric thermogram exhibiting a melting endotherm peak at 253° C.

8. Moxifloxacin hydrochloride Form C according to claim 7, characterized by having a differential scanning calorimetric thermogram as shown in FIG. 3.

9. Moxifloxacin hydrochloride Form C characterized by having a Raman spectrum with Raman peaks at 3094.48, 3079.19, 3052.84, 3038.86, 3012.81, 2997.21, 2964.58, 2934.40, 2879.86, 1741.20, 1618.72, 1547.70, 1490.01, 1462.68, 1430.60, 1393.53, 1372.62, 1354.07, 1337.13, 1314.47, 1302.62, 1277.88, 1226.72, 1207.46, 1189.47, 1164.50, 1104.89, 1030.51, 957.69, 939.73, 888.57, 831.46, 783.78, 723.06, 687.13, 541.70, 477.11, 425.87, 389.22, 306.92, 271.51, 228.03, 207.24, 140.22, 103.95, 75.76. $cm^{-1}$.

10. Moxifloxacin hydrochloride Form C according to claim 9, characterized by having a Raman spectrum as shown in FIG. 4.

11. The pharmaceutical composition comprising Moxifloxacin hydrochloride Form C according to claim 1, in combination with a pharmaceutically acceptable carrier.

12. A method of making Moxifloxacin hydrochloride Form C as defined in claim 1, comprising dissolving or suspending moxifloxacin base in methanol, treating the solution with methanolic hydrochloric acid; and isolating moxifloxacin hydrochloride Form C from the methanol.

13. The method according to claim 12, wherein the treatment with methanolic hydrochloric acid is carried out at a temperature from 0° C. to 30° C.

14. The method according to claim 12, wherein the moxifloxacin base is prepared by the steps of:
  i) Reacting propionic anhydride and boric acid with Ethyl-1-cyclopropyl-6-7-difluoro-8-methoxy-4-oxo-1,4-dihydro-3-quinolone carboxylate to obtain 1-cyclopropyl-6,7-difluoro-8-methoxy-4-oxo-1,4-dihydro-3-quinoline carboxylic acid-$O^3,O^4$ bis(propyloxy-O) borate;
  ii) Condensing the borate complex (I) with (S,S)-2,8-Diazabicyclo[4.3.0]nonane in an organic solvent to obtain the intermediate (4aS-Cis)-(1-cyclopropyl-7-(2,8-diazabicyclo[4.3.0]non-8-yl)-6-fluoro-8-methoxy-4-oxo-1,4-dihydro-3-quinoline carboxylic acid-$O^3,O^4$)bis(propyloxy-O)borate; and
  iii) hydrolyzing the intermediate (II) to get moxifloxacin base.

15. Moxifloxacin hydrochloride Form C prepared by a process according to claim 12.

\* \* \* \* \*